United States Patent [19]

Goldmann et al.

[11] Patent Number: 5,606,066
[45] Date of Patent: Feb. 25, 1997

[54] LIGHT ACTIVABLE "CAGED" 1-(2-NITROBENZYL)-SUBSTITUTED 1,4-DIHYDROPYRIDINES

[76] Inventors: Siegfried Goldmann, Am Osterholz 91, Wuppertal, Germany, D-42327; Martin Bechem, Hans-Böckler-Str. 102, Wuppertal, Germany, D-4211

[21] Appl. No.: 356,410

[22] PCT Filed: Jul. 3, 1993

[86] PCT No.: PCT/EP93/01720

§ 371 Date: May 1, 1995

§ 102(e) Date: May 1, 1995

[87] PCT Pub. No.: WO94/01405

PCT Pub. Date: Jan. 20, 1994

[30] Foreign Application Priority Data

Jul. 10, 1992 [DE] Germany .................. 42 22 770.4

[51] Int. Cl.$^6$ .................................................. C07D 211/86
[52] U.S. Cl. ................................................................ 546/321
[58] Field of Search ................................................ 546/321

[56] References Cited

FOREIGN PATENT DOCUMENTS

| 0071819 | 2/1983 | European Pat. Off. . |
|---|---|---|
| 0247345 | 12/1987 | European Pat. Off. . |
| 0255710 | 2/1988 | European Pat. Off. . |
| 0292161 | 11/1988 | European Pat. Off. . |
| 0330470 | 8/1989 | European Pat. Off. . |
| 2528425 | 12/1983 | France . |
| 1670827 | 3/1971 | Germany . |
| 2949491 | 6/1980 | Germany . |

*Primary Examiner*—Jane Fan
*Attorney, Agent, or Firm*—Jones & Askew

[57] ABSTRACT

Light-activable 1-(2-nitrobenzyl) substituted 1,4-dihydropyridines are provided, which are important intermediates for releasing highly effective 1,4-dihydropyridines. A process for preparing the same is also provided. The compounds may be used for facilitating and observing biological, physiological and pharmacological activities. The invention provides an approach for the synthesis of Ca-agonistic and Ca-antagonistic 1,4-dihydropyrimidines for monitoring calcium channel activity.

7 Claims, 1 Drawing Sheet

LIGHT ACTIVABLE "CAGED" 1-(2-NITROBENZYL)-SUBSTITUTED 1,4-DIHYDROPYRIDINES

This is a 371 of PCT/EP93/01720 filed Jul. 3, 1993 now WO94/01405

BACKGROUND OF THE INVENTION

The present application relates to light-activable 1-(2-nitrobenzyl) substituted 1,4-dihydropyridines, important intermediates for releasing highly effective 1,4-dihydropyridines, as well as a process for preparing the same. It is already known that 1-benzyl-substituted 1,4-dihydropyridines are used as chemotherapeutics (EP 330 470-A). See also DT 1,963,188-Q (17.12.69).

SUMMARY OF THE INVENTION

The present application relates to light-activable 1-(2nitrobenzyl) substituted 1,4-dihydropyridines, important intermediates for releasing highly effective 1,4-dihydropyridines, as well as a process for preparing the same. The compounds may be used for observing biological, physiological and pharmacological activities. For example, the invention provides an approach for the synthesis of Ca-agonistic and Ca-antagonistic 1,4-dihydropyrimidines for monitoring calcium channel activity.

DETAILED DESCRIPTION OF THE INVENTION

Figure 1:
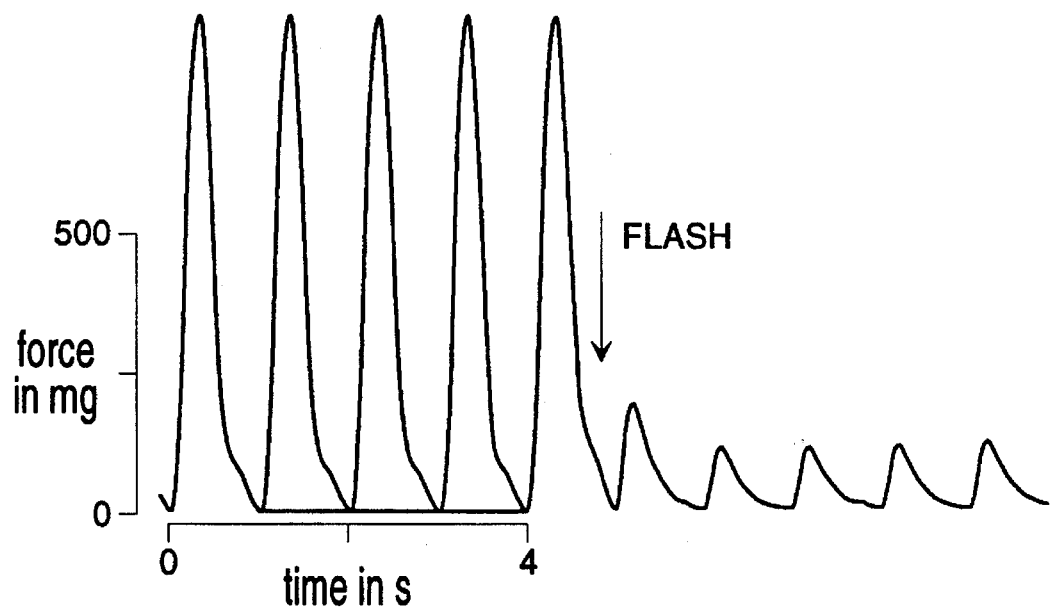
FIG. 1 shows the changes in force of muscle contraction after flash-activation of Ca-antagonist.

The invention is related to light-activable 1-(2-nitrobenzyl) substituted 1,4-dihydropyridines of the general formula (I)

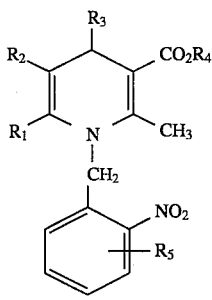

in which R1 represents hydrogen, cyano, formyl, hydrooxymethyl, methyl or aminoethoxymethyl; R2 represents cyano, nitro or a radical of the formula —CO—O—A, in which A represents a straight-chain or branched alkyl or alkenyl radical with 1 to 10 carbon atoms, which are optionally substituted by methylthio, methoxy, ethoxy, hydroxy or a benzyl-N(CH$_3$)—CH$_2$—CH$_2$-radical, or R1 and R2 together represent a lactone-ring of the formula (2)

R3 represents an aryl radical with 6 to 10 carbon atoms or a 5 to 7 membered unsaturated heterocyclic ring with up to 2 heteroatoms of the group S, N or O, both of which are optionally substituted by 1 to 3 identical or different substituents selected from halogen, nitro, trifluoromethyl, cyano, difluoromethoxy, a straight-chain or branched alkyl, alkoxy or alkylthio (each with 1 to 8 carbon atoms), benzyl, benzylthio, benzyloxy or phenoxy, or R3 represents a radical of the formula (3)

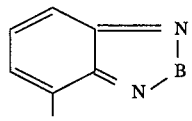

in which B represents O or S; R4 represents a straight-chain or branched alkyl or alkenyl radical with 1 to 10 carbon atoms, which are optionally substituted by methylthio, methoxy, ethoxy, hydroxy or a benzyl-N(CH$_3$)—CH$_2$—CH$_2$-radical; and R5 represents hydrogen, F—, Cl— Br—, hydroxy, carboxy-, a straight chain or branched alkyl, alkoxy- or alkoxycarbonyl radical, each with 1 to 8 carbon atoms, and salts thereof.

Compounds of the general formula (I) can be obtained as racemic mixtures or in the form of pure enantiomers.

Compounds of the general formula (I) are preferred, in which R1 represents hydrogen, cyano, hydrooxymethyl, methyl or aminoethoxymethyl; R2 represents cyano, nitro or a radical of the formula —CO—O—A, in which A represents a straight-chain or branched alkyl or alkenyl radical with 1 to 5 carbon atoms, which are optionally substituted by methoxy, ethoxy, hydroxy or a benzyl-N(CH$_3$)—CH$_2$—CH$_2$-radical, or R1 and R2 together represent a lactone-ring of the formula (2)

R3 represents phenyl, naphthyl, o-pridyl, m-pyridyl, p-pyridyl or thienyl which are optionally substituted by 1 to 2 identical or different substituents selected from fluorine, chlorine, bromine, nitro, trifluoromethyl, a straight-chain or branched alkyl, alkoxy or alkylthio (each with 1 to 6 carbon atoms), benzyl, benzylthio, benzyloxy or R3 represents a radical of the formula (3)

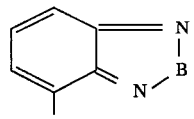

in which B represents O or S; R4 represents a straight-chain or branched alkyl or alkenyl radical with 1 to 5 carbon atoms, which are optionally substituted by methoxy, ethoxy, hydroxy or a benzyl-N(CH$_3$)—CH$_2$—CH$_2$-radical; and R5 represents hydrogen, F—, Cl— Br—, hydroxy, carboxy-, a straight chain or branched alkyl, alkoxy- or alkoxycarbonyl radical, each with 1 to 4 carbon atoms, and salts thereof.

Compounds of the general formula (I) are particularly preferred, in which R1 represents cyano, methyl or aminoethoxymethyl R2 represents cyano, nitro or a radical of the formula —CO—O—A, in which A represents a straight-chain or branched alkyl or alkenyl radical with 1 to 5 carbon atoms, which are optionally substituted by methoxy, ethoxy, hydroxy or a benzyl-N(CH$_3$)—CH$_2$—CH$_2$-radical, or R1 and R2 together represent a lactone-ring of the formula (2)

 (2)

R3 represents phenyl, naphthyl, o-pridyl, m-pyridyl or thienyl which are optionally substituted by 1 to 2 identical or different substituents selected from fluorine, chlorine, nitro, trifluoromethyl, a straight-chain or branched alkyl or alkoxy (each with 1 to 4 carbon atoms), benzyl, benzylthio, benzyloxy or R3 represents a radical of the formula (3)

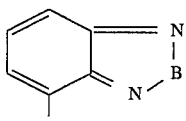 (3)

in which B represents O or S; R4 represents a straight-chain or branched alkyl or alkenyl radical with 1 to 5 carbon atoms, which are optionally substituted by methoxy, ethoxy, hydroxy or a benzyl-N(CH$_3$)—CH$_2$—CH$_2$-radical; and R5 represents hydrogen, F—, Cl— Br—, hydroxy, carboxy-, a straight chain or branched alkyl, alkoxy- or alkoxycarbonyl radical, each with 1 to 3 carbon atoms, and salts thereof.

In addition, a process for preparing the compounds of the general formula (I) according to the invention has been found, characterized in that:

[A] Aldehydes of the general formula (II)

 (II)

in which R3 has the above-mentioned meaning are reacted with compounds of the general formula (III) and (IV)

 (III)

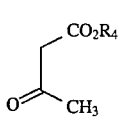 (IV)

in which R1, R2 and R4 have the above-mentioned meaning and compounds of the general formula (V), in which R4 has the above-mentioned meaning,

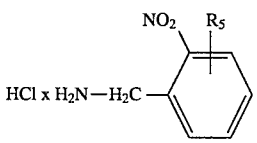

in inert solvents;

[B] ylidenecompounds of the general formula (VI) are reacted with a compound of formula (VII)

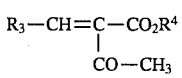 (VI)

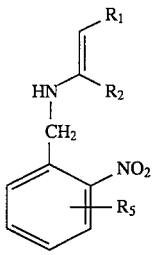 (VII)

in which R1, R2, R3, R4 and R5 have the above-mentioned meanings or compounds of the general formula (VIII) are reacted with compounds of formula (IX) in which R1, R2, R3, R4, and R5 have the above-mentioned meaning

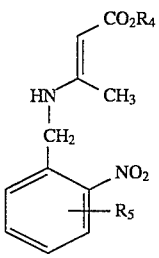 (VIII)

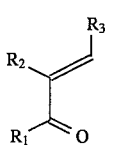 (IX)

inert solvents, optionally, in the presence of a catalyst; or

[C] compounds of the general formula (X) are reacted with compounds of the general formula (XI)

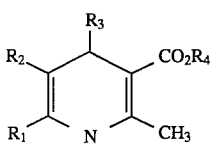 (X)

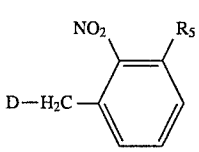 (XI)

in which R1, R2, R3, R4 and R5 have the above-mentioned meaning and D represents chlorine, bromine, iodine or a typical leaving group like tosylate or mesylate (for example), in inert solvents in the presence of a base.

The processes according to the invention can be illustrated, by way of example, by the following formula schemes:

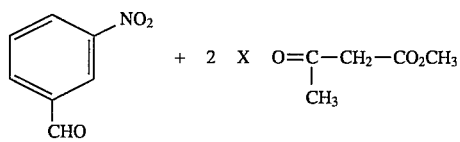 [A]

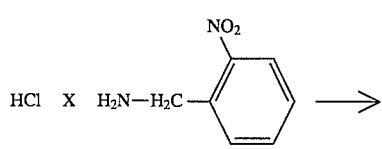

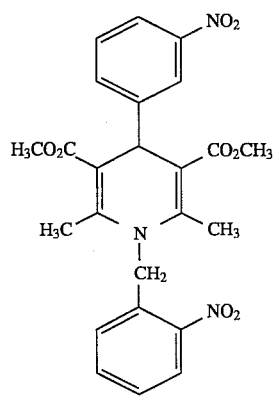

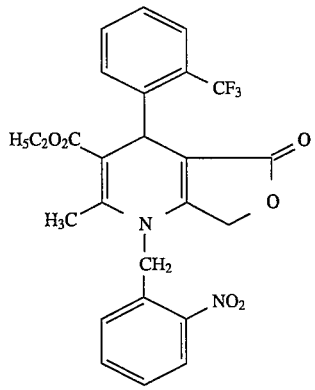

[B]

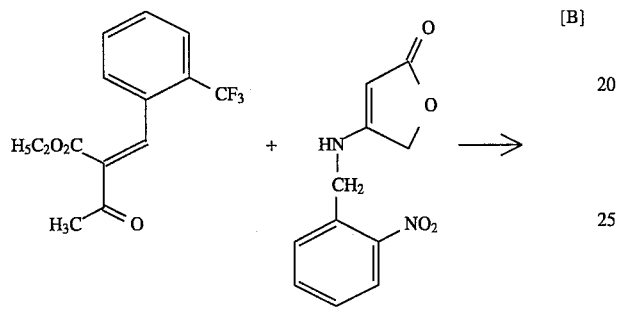

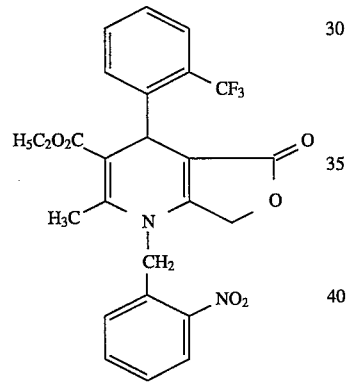

[C]

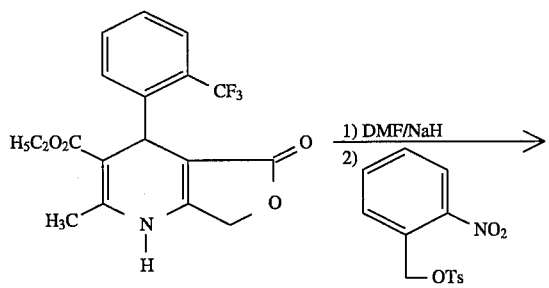

All inert organic solvents which are not altered under the reaction conditions are suitable for use as solvents in these processes. These solvents preferably include alcohols like methanol, ethanol or i-propanol, ether like diethylether, dioxan, tetrahydrofurane, glycolmono- or dimethylether, halogenated hydrocarbons like di-, tri- or tetrachloromethane, dichloroethylene, trichloroethylene or ethylacetate, toluene, acetonitrile, hexamethylphosphoric triamide, acetone or pyridine. It is likewise possible to use mixtures of the said solvents.

In process variant [C], in general alkali carbonates like sodium- or potassium carbonate or hydrides like sodium-, calcium- and potassium hydride are used as a base, with sodium hydride preferred.

In process variant [B], in general p-toluenesulfonic acid, sulfuric acid or hydrochloric acid can be used as a catalyst, with p-toluenesulfonic acid preferred.

The above preparation processes are given solely for clarification. The preparation of the compounds of the formula (I) is not restricted to these processes, but any modification of these processes is applicable in the same way for preparing the compounds according to the invention.

The compounds of the general formulae (II), (III), (IV), (V), (VI), (IX) and (X) are known or can be prepared in accordance with the customary methods.

The compounds of the general formula (VII) are novel, but can be prepared by reacting 2-nitrobenzylamin hydrochloride with alkyl acetoxyacetate in the presence of the above-mentioned bases, e.g., triethyl amine, in the above-mentioned solvents, e.g., methanol, at room temperature and atmospheric pressure. The intermediate is reacted with bases, e.g., potassium carbonate, to split off the acetate group yielding the cyclic tetramic acid.

The compounds of the general formula (VIII) are novel but can be prepared in a similar way to compounds (VII), but without the following base induced cyclization.

The substances according to this invention of formula (I) are useful intermediates for the synthesis of 1,4-dihydropyridines. The removal of the photolysable 2-nitrobenzyl group opens an easy approach for synthesis of Ca-agonistic and Ca-antagonistic 1,4-dihydropyridines. The activity of these substances may be increased upon light-induced activation which also presents a unique possibility for very localized, tissue-specific application of the active compound if focused illumination is used. Because of the very rapid release of the active compound—typically within 1 ms—these compounds are valuable tools for a variety of cell biological, physiological and pharmacological experiments. For example, light-induced competition measurements with other active 1,4-diohyrdopyridines in intact cells or cell fragments, may provide proof that the activity of Ca channels underlies a certain cell activity, and identify different tissue and cell specific Ca channels.

EXAMPLES

Utility Example

The-activity of the invented compounds has been demonstrated in the isolated, electrically stimulated preparation of the guinea pig heart papillary muscle. For the experiments, a small papillary muscle (diameter about 1 mm and length about 5 mm) from the right ventricle of a previously killed animal was prepared and mounted in an isolated tissue bath. The base of the muscle was fixed with two metal holders which also served for electrical stimulation. The other site of the muscle was connected with a force transducer for measurement of the force of contraction of the preparation. The contractions of the muscle were registered with a personal computer and stored for further analysis and plotting. The tissue bath was perfused with a heated (32° C., in single experiments with a temperature of 25° C.) physiological bath solution at a rate of 240 ml/h. The solution was perfused with carbogen (95% oxygen, 5% carbon dioxide) to adjust a pH value of 7.4. The used substances were dissolved in pure DMSO in a concentration of $10^2$ g/ml and stepwise diluted. At the final concentration the DMSO did not exceed 0.5% in the bath solution. In some experiments the sarcoplasmic reticulum was functionally removed by addition of 10 mM caffeine to the bath solution. During the experiment the papillary muscle is first incubated with a high concentration of the non-activated, caged 1,4-dihydropyridine (typically between 0.3 to 10 uM) under light protection. For optimum results, the incubation was performed by means of a Langendorff-type, retrograde perfusion of the total heart prior to the preparation of the papillary muscle. This ensured an equal distribution of the caged compound in the whole tissue of the heart including the papillary muscle.

After this incubation and equilibration phase of the papillary muscle, the caged 1,4-dihydropyridines were activated by a short light flash and the pharmacological activity of the released Ca-agonistic or Ca-antagonistic 1,4-dihydropyridines were recorded. For activation, a xenon flash lamp (with an energy of up to 350 J/flash, duration 1 ms) was used, which had been focused on the muscle preparation. FIG. 1 shows successive contractions during the flash activation of a caged Ca-antagonist (example nr. 3, concentration 3 uM, in the presence of 10 mM caffeine). After the flash, the amplitude of contractions rapidly declined with an exponential time constant of 300 to 500 ms.

Figure 2:
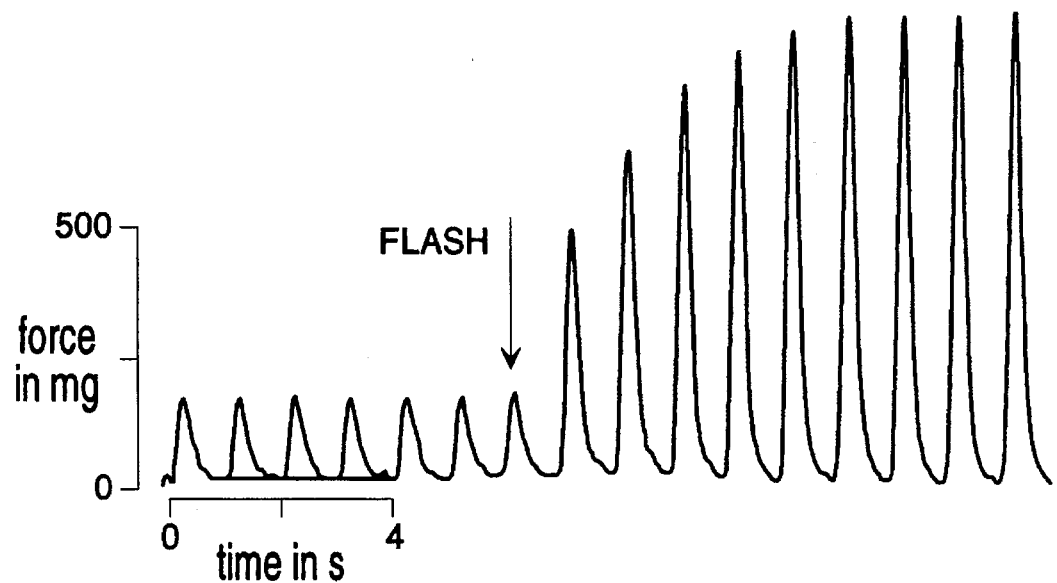
FIG. 2 shows the changes in force of muscle contraction after flash-activation of Ca-agonist.

FIG. 2 shows an example of an activation of a Ca-agonistic 1,4-dihydropyridine (example nr. 9). In this experiment, the compound was given during a Langendorff-type perfusion (concentration 3 uM, duration 40 min) prior to the preparation of the papillary muscle. After light-activation of the caged 1,4-dihydropyridine, the force of contraction is rapidly increased.

Examples of Starting Compounds

Example A

Methyl 3-(2-nitrobenzylamino)-crotonate

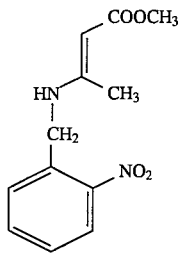

A mixture of 1.8 g (12 mmol) 2-nitrobenzyl amine (J. Hetercycl. Chem. 20, 1565 (1983)) and 1.4 (12 mmol) methyl acetoacetate and 2.2 ml triethyl amine in 25 ml methanol was stirred for 16 h at room temperature. The solvent was removed in vacuo and the residue was crystallized from methanol. Yield: 2 g (68%) of methyl 3-(2-nitrobenzylamino)-crotonate (mp: 64° C.).

Example B

N-(2-Nitrobenzyl)-tetramic acid

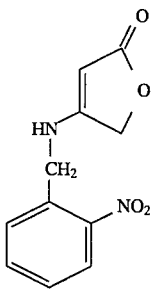

A mixture of 3 g (16 mmol) of 2-nitrobenzylaminehydrochloride, 3 g (16 mmol) of ethyl 4-acetoxy acetoacetate and 2.2 ml triethyl amine in 25 ml methanol was stirred for 16 h at room temperature. The solvent was removed, 50 ml $CH_2Cl_2$ was added, washed twice with water, dried with $Na_2SO_4$, and the solvent was removed. The residue was solved in dry methanol, $K_2CO_3$ was added and stirred for 2 h at room temperature. The solvent was removed, the residue stirred in $CH_2Cl_2$, twice washed with water, dried and evaporated. Yield: 40% of N-(2-nitrobenzyl)-tetramic acid (mp: 187° C.)

Preparation Examples

Example 1

Dimethyl 2,6-dimethyl-1-(2-nitrobenzyl)-4-(3-nitrophenyl)-1,4-dihydro-pyridine-3,5-dicarboxylate

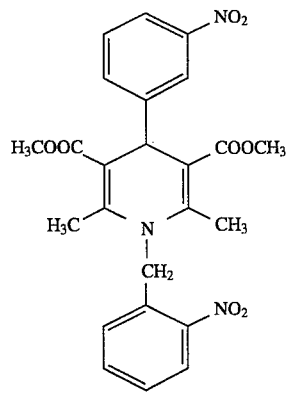

A mixture of 3 g (20 mmol) 3-nitrobenzaldehyde, 4.6 g (40 mmol) methyl acetoacetate and 3.7 g (20 mmol) 2-nitrobenzylamine HCl in 20 ml pyridine is heated for 6 h under reflux. After cooling the mixture is poured into water, extracted with $CH_2Cl_2$, died and the solvent removed. Chromatography yielded 1.7 g (18%) of dimethyl 2-6-dimethyl-1-(2-nitrobenzyl)-4-(3-nitrophenyl)-1,4-dihyrdo-pyridine-3,5-dicarboxylate (mp: 180° C.).

Example 2

Dimethyl 3-(2-chlorophenyl)-2,6-dimethyl-1-(2-nitrobenzyl)-1,4-dihydro-pyridine-3,5-dicarboxylate

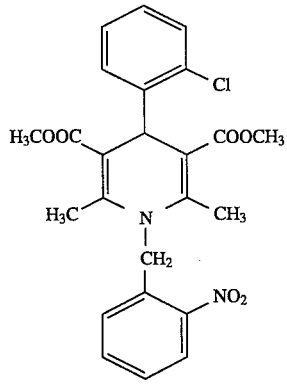

The compound is prepared in analogy to Example 1, but 2-chlorobenzaldehyde is used instead of 3-nitrobenzaldehyde. Yield 11% (mp: 144° C.).

Example 3

Ethyl 2-methyl-1-(2-nitrobenzyl)-5-oxo-4-(2-trifluoromethylphenyl)-1,4,5,7-tetrahydro-furo[3,4-b]pyridine-3-carboxylate

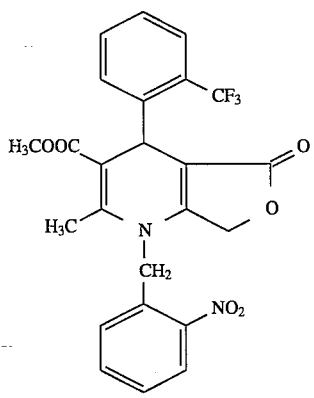

A mixture of 0.3 g (1.28 mmol) of N-(2-nitrobenzyl)-tetramic acid (Example B), 0.37 g (1.28 mmol) of ethyl-2-trifluoromethyl-benzylidene-acetoacetate and catalytical amounts of p-toluene sulfonic acid is heated for 40 h on 160° C. under argon. After cooling chromatography on $SiO_2$ (toluene/ethylacetate=7:3) yielded 110 mg (17%) of ethyl 2-methyl-1-(2-nitrobenzyl)-5-oxo-4-(2-trifluoromethylphenyl)-1,4,5,7-tetrahydro-furo[3,4-b]pyridine-3-carboxylate (mp: 233° C.).

Example 4

Methyl 2-methyl-4-(2-benzylthiophenyl)-1-(2-nitrobenzyl)-5-oxo-1,4,5,7-tetrahydrofuro[3,4-b]pyridine-3-carboxylate

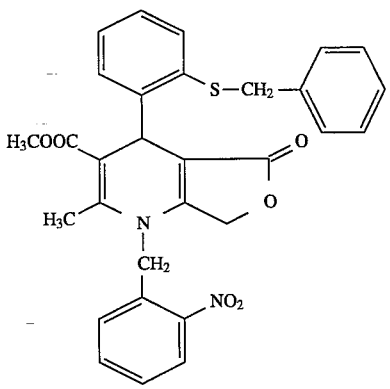

The compound is prepared in analogy to Example 3, with 2-benzylthiobenzaldehyde. Yield: 8% (mp: 149° C.).

Examples 5 and 6

Ethyl, methyl 2,6-dimethyl-1-(2-nitrobenzyl)-4-(3-nitrophenyl)-1,4-dihydro-pyridine-3,5-dicarboxylate.

(5)

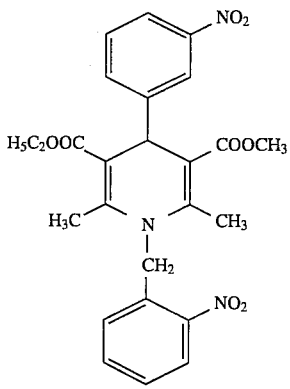

Diethyl 2,6-dimethyl-1 (2-nitrobenzyl)-4-(3-nitrophenyl)- 1,4-dihydro-pyridine-3,5-dicarboxylate.

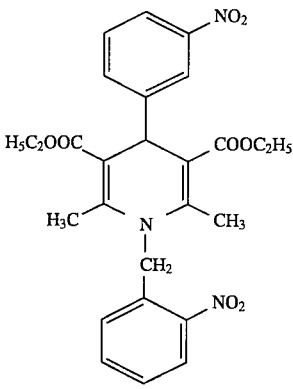

A mixture of 2.6 g (17 mmol) 3-nitrobenzaldehyde, 2 g (17 mmol) of methyl acetoacetate, 2.2 g (17 mmol) of ethyl acetoacetate and 3.2 g (17 mmol) of 2-nitrobenzylamine-hydrochloride in 20 ml pyridine is heated for 4 h under reflux. After work up in analogy to Example 1, and chromatography of the residue yielded 740 mg (9%) of ethyl, methyl 2,6-dimethyl-1-(2-nitrobenzyl)-4-(3-nitrophenyl)-1,4-dihydropyridine-3,5-dicarboxylate (mp: 150° C.), 240 mg (2.9%) of the symmetrical diethyl dicarboxylate (mp: 139° C.) and 405 mg of the compound of Example 1.

Examples 7 and 8

Isopropyl, methyl 4-(2,1,3-benzoxadiazol-4-yl)-2,6-dimethyl-1-(2-nitrobenzyl)-1,4-dihydropyridine-3,5-dicarboxylate

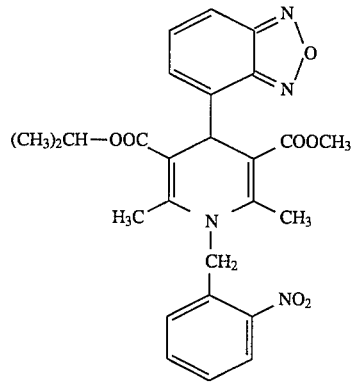

Dimethyl 4-(2,1,3-benzoxadiazol-4-yl)-2,6-dimethyl-1-(2-nitrobenzyl)-1,4-dihydropyridine-3,5-dicarboxylate

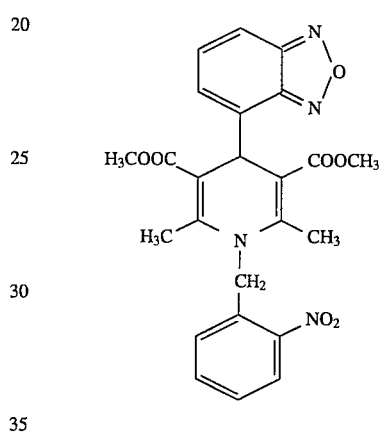

2,1,3-Benzoxadiazol-4-carbaldehyde is reacted in analogy to Example 5 and 6 with a 1:1 mixture of methyl acetoacetate and isopropyl acetoacetate. Chromatography (hexan/ethyl acetate=7:3) yielded 350 mg (4.1%) of isopropyl, methyl 4-(2,1,3-benzoxadiazol-4-yl)-2,6-dimethyl-1-(2-nitrobenzyl)-1,4-dihydropyridine-3,5-dicarboxylate (mp: 176° C.) and 284 mg (3.5%) of the corresponding dimethyl 4-(2,1,3-benzoxadiazol-4-yl)-2,6-dimethyl-1-(2-nitrobenzyl)-1,4-dihydropyridine-3,5-dicarboxylate (mp: 192° C.).

Example 9

Methyl 2,6-dimethyl-5-nitro-1-(2-nitrobenzyl)-4-(2-trifluoromethylphenyl)-1,4-dihydropyridine-3-carboxylate

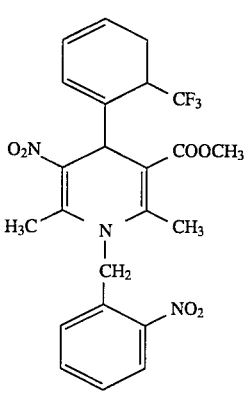

A mixture of 1.45 g (5.8 mmol) of intermediate A and 2-nitro-3-oxo-1-(2-trifluoromethylphenyl)-propene-1 is converted in analogy to Example 1 in pyridine to methyl 2,6-dimethyl-5-nitro-1-(2-nitrobenzyl)-4-(2-trifluoro-methylphenyl)-1,4-dihydropyridine-3-carboxylate (mp: 170° C., yellow crystals).

We claim:

1. 1-(2-nitrobenzyl) substituted 1,4-dihydropyridine of formula (I)

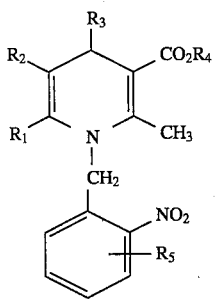

wherein $R_1$ represents hydrogen, cyano, formyl, hydroxymethyl, methyl or aminoethoxymethyl, $R_2$ represents cyano, nitro or a radical of the formula —CO—O—A, wherein A represents a straight-chain or branched alkyl or alkenyl radical with up to 10 carbon atoms, which is optionally substituted by methylthio, methoxy, ethoxy, hydroxy or a benzyl-N $(CH_3)$—$CH_2$—$CH_2$-radical, $R_3$ represents an aryl radical with 6 to 10 carbon atoms which is optionally substituted by 1 to 3 identical or different substituents selected from halogen, nitro, trifluoromethyl, cyano, difluoromethoxy, a straight-chain or branched alkyl, alkoxy or alkylthio (each with 1 to 8 carbon atoms), benzyl, benzylthio, benzyloxy or phenoxy, $R_4$ represents a straight-chain or branched alkyl or alkenyl radical with up to 10 carbon atoms, which is optionally substituted by methylthio, methoxy, ethoxy, hydroxy or a benzyl-N $(CH_3)$—$CH_2$—$CH_2$-radical, $R_5$ represents hydrogen, F, Cl, Br, hydroxy, carboxy, a straight-chain or branched alkyl, alkoxy or alkoxycarbonyl radical, each with up to 8 carbon atoms, and a salt thereof.

2. A compound of formula (I) as in claim 1 as a racemic mixture or in the form of a pure enantiomer.

3. A compound of formula (I) as in claim 1, wherein $R_1$ represents hydrogen, cyano, hydroxmethyl, methyl or aminoethoxymethyl, $R_2$ represents cyano, nitro or a radical of the formula —CO—O—A, wherein A represents a straight-chain or branched alkyl or alkenyl radical with up to 5 carbon atoms, which is optionally substituted by methoxy, ethoxy, hydroxy or a benzyl-N $(CH_3)$—$CH_2$—$CH_2$-radical, $R_3$ represents phenyl or naphthyl which is optionally substituted by 1 to 2 identical or different substituents selected from fluorine, chlorine, bromine, nitro, trifluoromethyl, a straight-chain or branched alkyl, alkoxy or alkylthio (each with 1 to 6 carbon atoms), benzyl, benzylthio, benzyloxy, $R_4$ represents a straight-chain or branched alkyl or alkenyl radical with up to 5 carbon atoms, which is optionally substituted by methoxy, ethoxy, hydroxy or a benzyl-N $(CH_3)$—$CH_2$—$CH_2$-radical, $R_5$ represents hydrogen, F, Cl, Br, hydroxy, carboxy, a straight-chain or branched alkyl, alkoxy or alkoxycarbonyl radical, each with up to 4 carbon atoms, and a salt thereof.

4. A compound of formula (I) as in claim 1, wherein $R_1$ represents cyano, methyl or aminoethoxymethyl, $R_2$ represents cyano, nitro or a radical of the formula —CO—O—A, wherein A represents a straight-chain or branched alkyl or alkenyl radical with up to 10 carbon atoms, which is optionally substituted by methylthio, methoxy, ethoxy, hydroxy or a benzyl-N $(CH_3)$—$CH_2$—$CH_2$-radical, $R_3$ represents phenyl or naphthyl which is optionally substituted by 1 to 2 identical or different substituents selected from fluorine, chlorine, nitro, trifluoromethyl, a straight-chain or branched alkyl or alkoxy (each with 1 to 4 carbon atoms), benzyl, benzylthio, benzyloxy, $R_4$ represents a straight-chain or branched alkyl radical with up to 5 carbon atoms, which is optionally substituted by methoxy, ethoxy, hydroxy or a benzyl-N-$(CH_3)$—$CH_2$—$CH_2$-radical, $R_5$ represents hydrogen, F, Cl, hydroxy, carboxy, a straight-chain or branched alkyl, alkoxy or alkoxycarbonyl radical, each with up to 3 carbon atoms, and a salt thereof.

5. The compound dimethyl 4-(2-chlorophenyl)-2,6-dimethyl-1-(2-nitrobenzyl)-1,4-dihydro-pyridine-3,5-dicarboxylate.

6. The compound methyl 2,6-dimethyl-5-nitro-1-(2-nitrobenzyl)-4-(2-trifluoromethylphenyl)-1,4-dihydropyridine-3-carboxylate.

7. A process for preparing a compound of formula (I) as in claim 1 in which an aldehyde of formula (II)

wherein $R_3$ has the above-mentioned meaning, is reacted with a compound of formulae (III) and (IV)

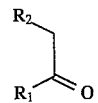

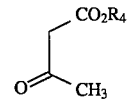

in which $R_1$, $R_2$ and $R_4$ have the above-mentioned meaning and a compound of formula (V), in which $R_5$ has the above-mentioned meaning,

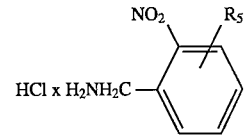

in an inert solvent.

* * * * *